United States Patent
Lubisch et al.

(10) Patent No.: US 8,202,870 B2
(45) Date of Patent: *Jun. 19, 2012

(54) SUBSTITUTED OXINDOLE DERIVATIVES, MEDICAMENTS CONTAINING THE LATTER AND USE THEREOF

(75) Inventors: Wilfried Lubisch, Heidelberg (DE); Thorsten Oost, Ludwigshafen (DE); Wolfgang Wernet, Ludwigshafen (DE); Wilfried Hornberger, Ludwigshafen (DE); Liliane Unger, Ludwigshafen (DE); Hervé Geneste, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 517 days.

This patent is subject to a terminal disclaimer.

(21) Appl. No.: 11/886,731

(22) PCT Filed: Mar. 23, 2006

(86) PCT No.: PCT/EP2006/002684
§ 371 (c)(1),
(2), (4) Date: Jan. 13, 2009

(87) PCT Pub. No.: WO2006/100081
PCT Pub. Date: Sep. 28, 2006

(65) Prior Publication Data
US 2009/0215790 A1    Aug. 27, 2009

Related U.S. Application Data

(60) Provisional application No. 60/664,899, filed on Mar. 24, 2005.

(30) Foreign Application Priority Data

Mar. 26, 2005   (DE) .................. 10 2005 014 904

(51) Int. Cl.
| A61K 31/496 | (2006.01) |
|---|---|
| A61K 31/497 | (2006.01) |
| A61K 31/506 | (2006.01) |
| C07D 401/14 | (2006.01) |
| C07D 407/14 | (2006.01) |
| C07D 409/14 | (2006.01) |

(52) U.S. Cl. ......... 514/252.11; 514/252.18; 514/252.19; 514/253.06; 514/253.09; 514/254.02; 514/254.09; 544/295; 544/357; 544/363; 544/364; 544/369; 544/373

(58) Field of Classification Search .............. None
See application file for complete search history.

(56) References Cited

U.S. PATENT DOCUMENTS

| 5,594,023 | A | 1/1997 | Wagnon et al. |
|---|---|---|---|
| 6,090,818 | A | 7/2000 | Foulon et al. |
| 6,596,732 | B2 | 7/2003 | Serradeil-Le Gal et al. |
| 6,624,164 | B2 | 9/2003 | Schoentjes et al. |
| 7,119,086 | B2 | 10/2006 | Di Malta et al. |
| 2003/0114683 | A1 | 6/2003 | Roux et al. |
| 2003/0162767 | A1 | 8/2003 | Roux et al. |
| 2004/0180878 | A1* | 9/2004 | Di Malta et al. ............. 514/218 |
| 2005/0070718 | A1* | 3/2005 | Lubisch et al. ............. 548/181 |
| 2009/0005397 | A1 | 1/2009 | Lubisch et al. |

FOREIGN PATENT DOCUMENTS

| CA | 2107348 A1 | 7/1993 |
|---|---|---|
| CA | 2593044 A1 | 7/2006 |
| WO | 9315051 A1 | 8/1993 |
| WO | 9518105 A1 | 7/1995 |
| WO | 9825901 A1 | 6/1998 |
| WO | 0155130 A2 | 8/2001 |
| WO | 0155134 A2 | 8/2001 |
| WO | 0164668 A2 | 9/2001 |
| WO | 0198295 A1 | 12/2001 |
| WO | 03008407 A2 | 1/2003 |
| WO | 2006005609 A2 | 1/2006 |
| WO | 2006072458 A2 | 7/2006 |

OTHER PUBLICATIONS

Banker et al. "Modern Pharmaceutics", 3rd Ed. p. 596 (1996).*
Wolff, Manfred E. Burger's Medicinal Chemistry, 5th Ed. Part 1, pp. 975-977 (1995).*
Thibonnier, Exp.OPin.Invest.Drugs, vol. 7(5), p. 729-740 (1998).*
Hays, New England Journal of Medicine, vol. 355(20), p. 2146-2148 (2006).*

* cited by examiner

*Primary Examiner* — Emily Bernhardt
(74) *Attorney, Agent, or Firm* — Lisa V. Mueller; Michael Best & Friedrich LLP

(57) ABSTRACT

The invention relates to novel oxindole derivatives of general formula (I), in which the substituents $R^1$, $R^2$, $R^3$, $Y^1$, $Y^2$, m, n, W, X, B and Z are defined as cited in claim 1, to medicaments containing said derivatives and to the use of the latter for the prophylaxis and/or treatment of vasopressin-dependent and/or oxytocin-dependent diseases

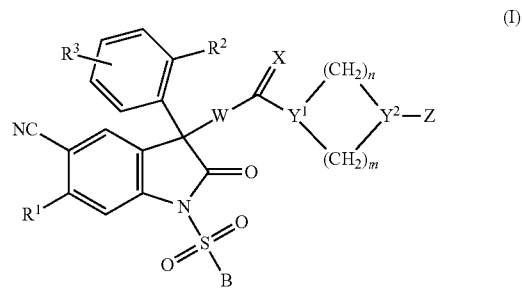

5 Claims, No Drawings

SUBSTITUTED OXINDOLE DERIVATIVES, MEDICAMENTS CONTAINING THE LATTER AND USE THEREOF

The present invention relates to novel oxindole derivatives, to medicaments comprising them and to their use for the treatment and/or prophylaxis of diseases.

Vasopressin (AVP) is an endogenous hormone which exerts various effects on organs and tissues. Vasopressin is related to oxytocin (OT), so that the two peptides are combined to form a vasopressin/oxytocin family. It is suspected that the vasopressin/oxytocin system is involved in various pathological states such as, for example, heart failure and high blood pressure. At present, three vasopressin receptors (V1a, V1b or V3 and V2 receptors) and one oxytocin receptor (OT receptor), via which vasopressin and oxytocin mediate their effects, are known. Antagonists of these receptors, especially including antagonists which bind specifically only one of the above receptors, represent novel therapeutic approaches to the treatment of diseases. (M. Thibonnier, Exp. Opin. Invest. Drugs 1998, 7(5), 729-740). It has been found, for example, that a selective antagonist of the vasopressin V1b receptor exerts anxiolytic and antidepressant effects in animal models (Griebel et al., PNAS 2002, 99, 6370; Serradeil-Le Gal et al., J. Pharm. Exp. Ther. 2002, 300, 1122). Since the models described have a certain predictive value for the clinical effects to be expected, antagonists of the V1b receptor are of particular interest for the treatment of emotional disturbances or disorders such as, for example, stress, anxiety states and/or depression.

Oxytocin is a hormone which is produced in neurosecretory neurons of the hypothalamus and—bound to neurophysins—is transported to the posterior pituitary lobe and is stored there. Oxytocin stimulates contraction of the uterine muscles and of the myoepithelial cells of the mammary gland (ejection of milk); the contractility of the uterus is altered by estrogens (promoting effect) and progestogens (inhibiting effect). Oxytocin is broken down by the enzyme oxytocinase. Oxytocin is used in obstetrics (e.g. for the induction of labor, in the event of postpartum uterine atony) (quoted from: Roche Lexikon Medizin 5th edition).

The present application describes novel substituted oxindoles which have an arylsulfonyl group in position 1. 1-Phenylsulfonyl-1,3-dihydro-2H-indol-2-ones have previously been described as ligands of vasopressin receptors. WO 93/15051, WO95/18105, WO 98/25901, WO 01/55130, WO 01/55134, WO 01/164668 and WO 1/98295 have described derivatives derived from the oxindole structure and having arylsulfonyl groups in position 1. These compounds differ essentially in the substitution in position 3.

In particular, WO 93/15051 and WO 98/25901 describe 1-phenylsulfonyl-1,3-dihydro-2H-indol-2-ones, in which the oxindole structure is substituted in position 3 by two alkyl radicals which may likewise be a cycloalkyl radical (spiro linkage), as ligands of vasopressin receptors. As alternative, the spiro ring may comprise heteroatoms such as oxygen and nitrogen (optionally with substituents).

WO 95/18105 describes 1-phenylsulfonyl-1,3-dihydro-2H-indol-2-ones which have a nitrogen atom in position 3 as ligands of vasopressin receptors. In addition, radicals which may be alkyl, cycloalkyl, phenyl or benzyl radicals are bonded in position 3 (in each case optionally with substituents).

Other publications, for example WO 01/55130, describe compounds which have nitrogen-containing rings (e.g. proline, homoproline, morpholine, tetrahydroisoquinoline, dihydroindole; in each case optionally with substituents) which are linked via their nitrogen atom to position 3 of the oxindole structure but which are substituted by phenylsulfonyl or phenyl groups (optionally with substituents) both in position 1 and in position 3 on the oxindole ring.

WO 03/008407 describes 1-phenylsulfonyloxindoles in which pyridylpiperazines are linked via an oxycarbonyl group to the oxindole in position 3.

It is an object of the present invention to provide novel compounds for the treatment or prophylaxis of various vasopressin-dependent or oxytocin-dependent diseases. It was intended that the compounds have a high and selective activity for one of the receptors from the vasopressin/oxytocin receptor family, especially the V1b receptor. It was further intended that the compounds show improvements compared with known compounds, especially higher selectivity in relation to binding to the V1a and OT receptors, better metabolic stability and better pharmacological activity in suitable models which enable prognostic statements to be made about use in therapy.

The object is achieved by compounds of the general formula (I)

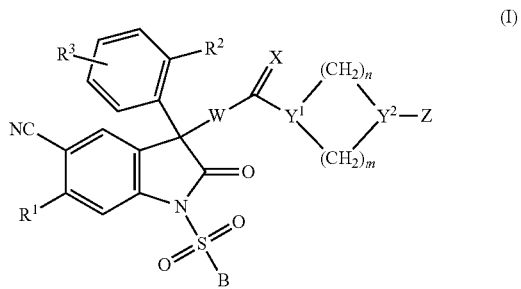

in which
$R^1$ is hydrogen, $C_1$-$C_4$-alkyl, O—($C_1$-$C_4$-alkyl), Cl or F;
$R^2$ is O—$C_1$-$C_4$-alkyl, $C_1$-$C_6$-alkyl, or Cl;
$R^3$ is hydrogen, F, Cl, $(CH_2)_{0-2}$—CN, $CF_3$, $OCF_3$, $CONH_2$, $CONH(C_1$-$C_4$-alkyl), $CON(C_1$-$C_4$-alkyl)($C_1$-$C_4$-alkyl), NHCHO, $NHCONH_2$, $NH(C_0$-$C_4$-alkylene)$CONH_2$, $NH(C_0$-$C_4$-alkylene)$CONH(C_1$-$C_4$-alkyl), $NHCOCH_3$, $NO_2$, $(CH_2)_{1-2}$—OH, O—$C_1$-$C_6$-alkyl, $(CH_2)_{1-2}$—O—$C_1$-$C_4$-alkyl, O—$C_0$-$C_4$-alkylene-phenyl, phenyl, $C_1$-$C_6$-alkyl, $C_2$-$C_6$-alkenyl or $C_2$-$C_6$-alkynyl;
B is a mono-, bi- or tricyclic heteroaromatic ring system which may consist of 5, 6, 7, 8, 9, 10, 11, 12, 13, 14 or 15 ring members, where the ring members may, besides carbon, also be one, two, three, four, five, six or seven identical or different heteroatoms independently of one another selected from the group consisting of O, N and S, and the hetero members may be present in one, in two or distributed in the rings, where the ring system can comprise a maximum simultaneously of one S ring member, two O ring members and 4 N ring members, and where the ring system comprises, however, at least one S, O or N ring member;
where
B may additionally be substituted by one, two, three or four radicals selected from the group consisting of $R^4$, $R^5$, $R^6$ and $R^7$, where $R^4$, $R^5$, $R^6$ and $R^7$ may independently of one another and independently of their respective occurrence be selected from the group consisting of hydrogen, Cl, Br, I, F, $(CH_2)_{0-2}$—CN, $CF_3$, $OCF_3$, $CONH_2$, $CONH(C_1$-$C_4$-alkyl), $CON(C_1$-$C_4$-alkyl)($C_1$-$C_4$-alkyl), NHCHO, $NH(C_{0-4}$-alkylene)

CONH($C_1$-$C_4$-alkyl), NHCOCH$_3$, NO$_2$, OH, O—$C_1$-$C_4$-alkyl, (CH$_2$)$_{0-2}$—O—(CH$_2$)$_{0-3}$—CH$_3$, O—$C_0$-$C_4$-alkylene-phenyl, phenyl, $C_1$-$C_6$-alkyl, $C_2$-$C_6$-alkenyl and $C_2$-$C_6$-alkynyl;

W is O, CH$_2$ or NH;
X is O, NH or N—CN; and
$Y^1$ is C or N;
$Y^2$ is C or N;
m is 1 or 2;
n is 2 or 3;
Z is a mono-, bi- or tricyclic heteroaromatic ring having 2, 3, 4, 5, 6, 7, 8, 9, 10, 11, 12, 13 or 14 C atoms as ring members and 1, 2, 3, 4, 5, 6 or 7 identical or different heteroatoms which are selected independently of one another from the group consisting of N, S and O, as ring members,
  where Z may additionally be substituted by the radicals $R^8$, $R^9$ and $R^{10}$, where $R^8$, $R^9$ and $R^{10}$ may each independently of one another have the meanings mentioned below, namely
  $R^8$ may be hydrogen, Cl, Br, I, F, (CH$_2$)$_{0-2}$—CN, CF$_3$, OCF$_3$, CONH$_2$, COOH, CONH($C_1$-$C_4$-alkyl), CON($C_1$-$C_4$-alkyl)($C_1$-$C_4$-alkyl), NHCHO, NHCONH$_2$, NH($C_0$-$C_4$-alkylene)CONH$_2$, NH($C_0$-$C_4$-alkylene)CONH($C_1$-$C_4$-alkyl), NHCOCH$_3$, NO$_2$, (CH$_2$)$_{0-2}$—OH, O—$C_1$-$C_6$-alkyl, (CH$_2$)$_{1-2}$—O—$C_1$-$C_4$-alkyl, O—$C_0$-$C_4$-alkylene-phenyl, phenyl, $C_1$-$C_6$-alkyl, $C_2$-$C_6$-alkenyl and $C_2$-$C_6$-alkynyl, NH$_2$, NH($C_1$-$C_4$-alkyl) or N($C_1$-$C_4$-alkyl)($C_1$-$C_4$-alkyl);
  $R^9$ may be hydrogen, Cl, Br, I, F, (CH$_2$)$_{0-2}$—CN, CF$_3$, OCF$_3$, CONH$_2$, COOH, CONH($C_1$-$C_4$-alkyl), CON($C_1$-$C_4$-alkyl)($C_1$-$C_4$-alkyl), NHCHO, NHCONH$_2$, NH($C_0$-$C_4$-alkylene)CONH$_2$, NH($C_0$-$C_4$-alkylene)CONH($C_1$-$C_4$-alkyl), NHCOCH$_3$, NO$_2$, (CH$_2$)$_{0-2}$—OH, O—$C_1$-$C_6$-alkyl, (CH$_2$)$_{1-2}$—O—$C_1$-$C_4$-alkyl, O—$C_0$-$C_4$-alkylene-phenyl, phenyl, $C_1$-$C_6$-alkyl, $C_2$-$C_6$-alkenyl and $C_2$-$C_6$-alkynyl, NH$_2$, NH($C_1$-$C_4$-alkyl) or N($C_1$-$C_4$-alkyl)($C_1$-$C_4$-alkyl);
  and
  $R^{10}$ may be hydrogen, Cl, F, $C_1$-$C_6$-alkyl, $C_2$-$C_6$-alkenyl, $C_2$-$C_6$-alkynyl or $C_0$-$C_4$-alkylene-phenyl;

and their tautomeric, enantiomeric and/or diastereomeric forms, and their prodrugs, and the physiologically tolerated salts of said compounds.

A preferred embodiment of the invention relates to compounds of the general formula (I), in which the variables independently of one another have the following meanings:
$R^1$ is hydrogen, $C_1$-$C_4$-alkyl, O—($C_1$-$C_4$-alkyl), Cl or F;
$R^2$ is O—$C_1$-$C_4$-alkyl, $C_1$-$C_6$-alkyl, or Cl;
$R^3$ is hydrogen, F, Cl, (CH$_2$)$_{0-2}$—CN, CF$_3$, OCF$_3$, CONH$_2$, CONH($C_1$-$C_4$-alkyl), CON($C_1$-$C_4$-alkyl)($C_1$-$C_4$-alkyl), NHCHO, NHCONH$_2$, NH($C_0$-$C_4$-alkylene)CONH$_2$, NH($C_0$-$C_4$-alkylene)CONH($C_1$-$C_4$-alkyl), NHCOCH$_3$, NO$_2$, (CH$_2$)$_{1-2}$—OH, O—$C_1$-$C_6$-alkyl, (CH$_2$)$_{1-2}$—O—$C_1$-$C_4$-alkyl, O—$C_0$-$C_4$-alkylene-phenyl, phenyl, $C_1$-$C_6$-alkyl, $C_2$-$C_6$-alkenyl or $C_2$-$C_6$-alkynyl;
B is a mono-, bi- or tricyclic heteroaromatic ring system which may consist of 5, 6, 7, 8, 9, 10, 11, 12, 13, 14 or 15 ring members, where the ring members may, besides carbon, also be one, two, three, four, five, six or seven identical or different heteroatoms independently of one another selected from the group consisting of O, N and S, and the hetero members may be present in one, in two or distributed in the rings, where the ring system may comprise a maximum simultaneously of one S ring member, two O ring members and 4 N ring members, and where the ring system comprises, however, at least one S, O or N ring member,
  where B may additionally be substituted by one, two, three or four radicals selected from the group consisting of $R^4$, $R^5$, $R^6$ and $R^7$, where $R^4$, $R^5$, $R^6$ and $R^7$ are selected independently of one another and independently of their respective occurrence from the group consisting of hydrogen, Cl, Br, I, F, (CH$_2$)$_{0-2}$—CN, CF$_3$, OCF$_3$, CONH$_2$, CONH($C_1$-$C_4$-alkyl), CON($C_1$-$C_4$-alkyl)($C_1$-$C_4$-alkyl), NHCHO, NH($C_{0-4}$-alkylene)CONH($C_1$-$C_4$-alkyl), NHCOCH$_3$, NO$_2$, OH, O—$C_1$-$C_4$-alkyl, (CH$_2$)$_{0-2}$—O—(CH$_2$)$_{0-3}$—CH$_3$, O—$C_0$-$C_4$-alkylene-phenyl, phenyl, $C_1$-$C_6$-alkyl, $C_2$-$C_6$-alkenyl and $C_2$-$C_6$-alkynyl;

W is O, CH$_2$ or NH;
X is O, NH or N—CN;
$Y^1$ is C or N;
$Y^2$ is C or N;
m is 1 or 2;
n is 2 or 3;
Z is a radical selected from the group consisting of the radicals

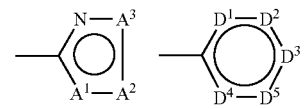

or
Z is a radical selected from the group consisting of the benzimidazolyl, benzofuranyl, benzothiazolyl, benzoxazolyl, indolyl, 5-azaindolyl, 6-azaindolyl, 7-azaindolyl, imidazo[1,5-a]pyridinyl and pyrazolo[1,5-a]pyridinyl radicals, where
$A^2$ and $A^3$ may independently of one another be N or C;
$A^1$ may be N, C, O or S;
$D^1$, $D^2$, $D^3$, $D^4$ and $D^5$ may independently of one another be C or N, where at least one of the variables $D^1$, $D^2$, $D^3$, $D^4$ or $D^5$ is N,
and where Z may in each case additionally be substituted by the radicals $R^8$, $R^9$ and $R^{10}$, where $R^8$, $R^9$ and $R^{10}$ may each independently of one another have the meanings mentioned below, namely
  $R^8$ may be hydrogen, Cl, Br, I, F, (CH$_2$)$_{0-2}$—CN, CF$_3$, OCF$_3$, CONH$_2$, COOH, CONH($C_1$-$C_4$-alkyl), CON($C_1$-$C_4$-alkyl)($C_1$-$C_4$-alkyl), NHCHO, NHCONH$_2$, NH($C_0$-$C_4$-alkylene)CONH$_2$, NH($C_0$-$C_4$-alkylene)CONH($C_1$-$C_4$-alkyl), NHCOCH$_3$, NO$_2$, (CH$_2$)$_{0-2}$—OH, O—$C_1$-$C_6$-alkyl, (CH$_2$)$_{1-2}$—O—$C_1$-$C_4$-alkyl, O—$C_0$-$C_4$-alkylene-phenyl, phenyl, $C_1$-$C_6$-alkyl, $C_2$-$C_6$-alkenyl and $C_2$-$C_6$-alkynyl, NH$_2$, NH($C_1$-$C_4$-alkyl) or N($C_1$-$C_4$-alkyl)($C_1$-$C_4$-alkyl);
  $R^9$ may be hydrogen, Cl, Br, I, F, (CH$_2$)$_{0-2}$—CN, CF$_3$, OCF$_3$, CONH$_2$, COOH, CONH($C_1$-$C_4$-alkyl), CON($C_1$-$C_4$-alkyl)($C_1$-$C_4$-alkyl), NHCHO, NHCONH$_2$, NH($C_0$-$C_4$-alkylene)CONH$_2$, NH($C_0$-$C_4$-alkylene)CONH($C_1$-$C_4$-alkyl), NHCOCH$_3$, NO$_2$, (CH$_2$)$_{0-2}$—OH, O—$C_1$-$C_6$-alkyl, (CH$_2$)$_{1-2}$—O—$C_1$-$C_4$-alkyl, O—$C_0$-$C_4$-alkylene-phenyl, phenyl, $C_1$-$C_6$-alkyl, $C_2$-$C_6$-alkenyl and $C_2$-$C_6$-alkynyl, NH$_2$, NH($C_1$-$C_4$-alkyl) or N($C_1$-$C_4$-alkyl)($C_1$-$C_4$-alkyl);
  and
  $R^{10}$ may be hydrogen, Cl, F, $C_1$-$C_6$-alkyl, $C_2$-$C_6$-alkenyl, $C_2$-$C_6$-alkynyl or $C_0$-$C_4$-alkylene-phenyl;

and their tautomeric, enantiomeric and/or diastereomeric forms, and their prodrugs, and the physiologically tolerated salts of said compounds.

A further preferred embodiment of the invention relates to compounds of the general formula (I), in which the variables independently of one another have the following meanings:

$R^1$ is hydrogen;
B is a radical selected from the group consisting of the imidazolyl, thienyl, furanyl, pyrrolyl, thiazolyl, isoxazolyl, oxazolyl, 1,2,3-triazolyl, 1,3,4-triazolyl, thiadiazolyl, pyridyl, pyrimidinyl, pyrazinyl, phthalazinyl, benzimidazolyl, quinolinyl, isoquinolinyl, quinoxalinyl, quinazolinyl, benzothiazolyl, benzofuranyl, benzothiophenyl and indolyl radicals, and the selected radical may be substituted by one, two, three or four radicals selected from the group consisting of the radicals $R^4$, $R^5$, $R^6$ and $R^7$, where $R^4$, $R^5$, $R^6$ and $R^7$ are selected independently of one another and independently of their respective occurrence from the group consisting of hydrogen, F, Cl, CN, $NO_2$, O—$C_1$-$C_4$-alkyl, $(CH_2)_{1-2}$—O—$(CH_2)_{0-2}$—$CH_3$ and $C_1$-$C_6$-alkyl;
$R^2$ is O—$C_1$-$C_4$-alkyl, $C_1$-$C_6$-alkyl, or Cl;
$R^3$ is hydrogen, F, Cl, $CF_3$, O$C_1$-$C_4$-alkyl or $C_1$-$C_4$-alkyl;
W is O, NH or $CH_2$;
X is O, NH or N—CN;
$Y^1$ is C or N;
$Y^2$ is C or N;
m is 1 or 2;
n is 2 or 3;
Z is a radical selected from the group consisting of the radicals

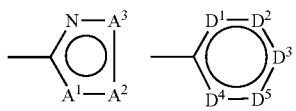

or
Z is a radical selected from the group consisting of the benzimidazolyl, benzofuranyl, benzothiazolyl, benzoxazolyl, indolyl, 5-azaindolyl, 6-azaindolyl, 7-azaindolyl, imidazo[1,5-a]pyridinyl and pyrazolo[1,5-a]pyridinyl radicals,
where
$A^2$ and $A^3$ may independently of one another be N or C;
$A^1$ may be N, C, O or S;
$D^1$, $D^2$, $D^3$, $D^4$ and $D^5$ may independently of one another and independently of their respective occurrence be C or N, but where at least one of the variables $D^1$, $D^2$, $D^3$, $D^4$ or $D^5$ is N,
and where
Z may in each case additionally be substituted by the radicals $R^8$, $R^9$ and $R^{10}$, where $R^8$, $R^9$ and $R^{10}$ may independently of one another have the following meanings, namely
$R^8$ may be hydrogen, Cl, F, CN, $CF_3$, $OCF_3$, $CONH_2$, $NHCONH_2$, $NHCOCH_3$, $NO_2$, OH, O—$C_1$-$C_4$-alkyl, $C_1$-$C_6$-alkyl, $NH_2$, NH($C_1$-$C_4$-alkyl) or N($C_1$-$C_4$-alkyl)($C_1$-$C_4$-alkyl);
$R^9$ may be hydrogen, Cl, F, CN, $CF_3$, $OCF_3$, $CONH_2$, $NHCONH_2$, $NHCOCH_3$, $NO_2$, OH, O—$C_1$-$C_4$-alkyl, $C_1$-$C_6$-alkyl, $NH_2$, NH($C_1$-$C_4$-alkyl) or N($C_1$-$C_4$-alkyl)($C_1$-$C_4$-alkyl);
$R^{10}$ may be hydrogen, F, Cl or $C_1$-$C_4$-alkyl, and their tautomeric, enantiomeric and/or diastereomeric forms, and their prodrugs, and the physiologically tolerated salts of said compounds.

A further preferred embodiment of the invention relates to compounds of the general formula (I), in which the variables independently of one another have the following meanings:

$R^1$ is hydrogen,
$R^2$ is $OCH_2CH_3$,
$R^3$ is hydrogen,
B is a cyclic radical selected from the group consisting of the quinolinyl, thienyl, pyridyl and pyrimidinyl radicals, which may each be substituted by the radicals $R^4$ and $R^5$, where $R^4$ and $R^5$ are selected independently of one another from the group consisting of hydrogen, F, Cl, CN, $NO_2$, O—$C_1$-$C_4$-alkyl and $C_1$-$C_6$-alkyl;
W is O, $CH_2$ or NH;
X is CO, NH or N—CN;
$Y^1$ is C or N;
$Y^2$ is C or N;
m is 2;
n is 2;
Z is a radical selected from the group consisting of the radicals

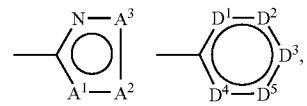

where
$A^2$ and $A^3$ may independently of one another be N or C;
$A^1$ may be N, C, O or S;
$D^1$, $D^2$, $D^3$, $D^4$ and $D^5$ may independently of one another be C or N, but where at least one of the variables $D^1$, $D^2$, $D^3$, $D^4$ or $D^5$ is N,
and where
Z may in each case be substituted by the radicals $R^8$, $R^9$ and $R^{10}$, where $R^8$, $R^9$ and $R^{10}$ may independently of one another have the following meanings, namely
$R^8$ may be hydrogen, Cl, F, CN, $CF_3$, $OCF_3$, $CONH_2$, $NHCOCH_3$, $NO_2$, OH, OC—$C_1$-$C_4$-alkyl, $C_1$-$C_4$-alkyl, $NH_2$, NH($C_1$-$C_4$-alkyl) or N($C_1$-$C_4$-alkyl)($C_1$-$C_4$-alkyl);
$R^9$ may be hydrogen, F, Cl, $OCH_3$ or $C_1$-$C_4$-alkyl;
$R^{10}$ is hydrogen;
and their tautomeric, enantiomeric and/or diastereomeric forms, and their prodrugs, and the physiologically tolerated salts of said compounds.

A further preferred embodiment of the invention relates to compounds of the general formula (I), in which the variables independently of one another have the following meanings:

$R^1$ is hydrogen;
$R^2$ is $OCH_2CH_3$;
$R^3$ is hydrogen;
B is a cyclic radical selected from the group consisting of the quinolinyl, thienyl, pyridyl and pyrimidinyl radicals, which may each be substituted by the radicals $R^4$ and $R^5$, where $R^4$ and $R^5$ are selected independently of one another from the group consisting of hydrogen, F, Cl, CN, $NO_2$, O—$C_1$-$C_4$-alkyl and $C_1$-$C_6$-alkyl;
W is O, $CH_2$ or NH;
X is CO or NH;
$Y^1$ is N;
$Y^2$ is N;
m is 2;
n is 2;

Z is a radical selected from the group consisting of the radicals

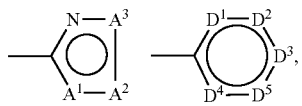

where
A² and A³ may independently of one another be N or C;
A¹ may be N, C, O or S;
D¹, D², D³, D⁴ and D⁵ may independently of one another be C or N,
where at least one of the variables $D^1$, $D^2$, $D^3$, $D^4$ or $D^5$ is N,
and where Z may in each case be substituted by the radicals $R^8$, $R^9$ and $R^{10}$, where $R^8$, $R^9$ and $R^{10}$ may independently of one another have the following meanings, namely
$R^8$ may be hydrogen, Cl, F, CN, $CF_3$, $OCF_3$, $CONH_2$, $NHCOCH_3$, $NO_2$, OH, OC—$C_1$-$C_4$-alkyl, $C_1$-$C_4$-alkyl, $NH_2$, $NH(C_1$-$C_4$-alkyl) or $N(C_1$-$C_4$-alkyl)($C_1$-$C_4$-alkyl);
$R^9$ may be hydrogen, F, Cl, $OCH_3$ or $C_1$-$C_4$-alkyl;
$R^{10}$ is hydrogen;
and their tautomeric, enantiomeric and/or diastereomeric forms, and their prodrugs, and the physiologically tolerated salts of said compounds.

A further preferred embodiment of the invention relates to compounds of the general formula (I) having a binding affinity Ki for the vasopressin V1b receptor subtype of less than about 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM.

A further preferred embodiment of the invention relates to compounds of the general formula (I), which have a selectivity for the vasopressin V1b receptor subtype vis-à-vis the vasopressin V1a receptor subtype, the quotient of Ki(V1a)/Ki(V1b) being greater than 1.

A further preferred embodiment of the invention relates to compounds of the general formula (I), which have a selectivity for the vasopressin V1b receptor subtype vis-à-vis the vasopressin V2 receptor subtype, the quotient of Ki(V2)/Ki(V1b) being greater than 1.

A further preferred embodiment of the invention relates to compounds of the general formula (I), which have a selectivity for the vasopressin V1b receptor subtype vis-à-vis the oxytocin (OT) receptor, the quotient of Ki(OT)/Ki(V1b) being greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and a selectivity for the vasopressin V1b receptor subtype vis-à-vis the vasopressin V1a receptor subtype, the quotient of Ki(V1a)/Ki(V1b) being greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and a selectivity for the vasopressin V1b receptor subtype vis-à-vis the vasopressin V2 receptor subtype, the quotient of Ki(V2)/Ki(V1b) being greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and a selectivity for the vasopressin V1b receptor subtype vis-à-vis the oxytocin (OT) receptor, the quotient of Ki(OT)/Ki(V1b) being greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and selectivities for the vasopressin V1b receptor subtype vis-à-vis the vasopressin V1a receptor subtype and the vasopressin V2 receptor subtype, the quotients of Ki(V1a)/Ki(V1 b) and Ki(V2)/Ki(V1b) being in each case greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and simultaneous selectivities for the vasopressin V1b receptor subtype vis-à-vis the vasopressin V1a receptor subtype and the oxytocin (OT) receptor, the quotients of Ki(V1a)/Ki(V1b) and Ki(OT)/Ki(V1b) being in each case greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and simultaneous selectivities for the vasopressin V1b receptor subtype vis-à-vis the vasopressin V2 receptor subtype and the oxytocin (OT) receptor, the quotients of Ki(V2)/Ki(V1b) and Ki(OT)/Ki(V1b) being in each case greater than 1.

A further preferred embodiment of the invention relates to compounds of the general formula (I), which have a binding affinity Ki for the vasopressin V1b receptor subtype of less than 100 nM, preferably not more than 50 nM, e.g. from 0.01 nM to less than 100 nM, or from 0.1 nM to less than 100 nM or from 10 nM to less than 100 nM or from 0.1 nM to 50 nM or from 1 nM to 50 nM, and simultaneous selectivities for the vasopressin V1b receptor subtype vis-à-vis the vasopressin V1a receptor subtype, the vasopressin V2 receptor subtype and the oxytocin (OT) receptor, the quotients of Ki(V1a)/Ki(V1b), Ki(V2)/Ki(V1b) and Ki(OT)/Ki(V1b) being in each case greater than 1.

A further aspect of the present invention relates to compounds of the general formula (I) for use as medicament.

A further aspect of the present invention relates to a medicament comprising at least one compound of the general formula (I).

A further aspect of the present invention relates to the use of at least one compound of the general formula (I) for producing a medicament for the treatment and/or prophylaxis of vasopressin-dependent and/or oxytocin-dependent diseases.

A further aspect of the present invention relates to the use of at least one compound of the general formula (I) for producing a medicament for the treatment and/or prophylaxis of at least one disorder selected from the group consisting of diabetes insipidus, nocturnal enuresis, incontinence, diseases in which blood coagulation disorders occur, and for delaying micturition.

A further aspect of the present invention relates to the use of at least one compound of the general formula (I) for producing a medicament for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplasie), ischemias of the heart, disorders of the renal system, edemas, renal vasospasm, necrosis of the renal cortex, hyponatremia, hypokalemia, Schwartz-Bartter syndrome, disorders of the gatrointestinal tract, gastritic vasospasm, hepatocirrhosis, gastric and intestinal ulcer, emesis, emesis occurring during chemotherapy, and travel sickness.

A further aspect of the present invention relates to the use of at least one compound of the general formula (I) for producing a medicament for the treatment and/or prophylaxis of affective disorders.

A further aspect of the present invention relates to the use of at least one compound of the general formula (I) for producing a medicament for the treatment and/or prophylaxis of anxiety disorders and stress-dependent anxiety disorders.

A further aspect of the present invention relates to the use of at least one compound of the general formula (I) for producing a medicament for the treatment and/or prophylaxis of memory impairments and/or Alzheimer's disease.

A further aspect of the present invention relates to the use of at least one compound of the general formula (I) for producing a medicament for the treatment and/or prophylaxis of psychoses and/or psychotic disorders.

A further aspect of the present invention relates to the use of at least one compound of the general formula (I) for producing a medicament for the treatment and/or prophylaxis of Cushing's syndrome.

A further aspect of the present invention relates to the use of at least one compound of the general formula (I) as described above for producing a medicament for the treatment of sleep disorders.

A further aspect of the present invention relates to the use of at least one compound of the general formula (I) as described above for producing a medicament for the treatment and/or prophylaxis of depressive disorders.

A further aspect of the present invention relates to the methods for the therapeutic and/or prophylactic treatment of a mammal requiring a treatment by administering an effective amount of at least one compound of the general formula (I) for the treatment of at least one disease as described above.

In a preferred embodiment of the method described above the mammal is a human, a nonhuman animal or a nonhuman transgenic animal.

A further aspect of the present invention relates to a process for preparing compounds of the general formula (I), wherein the compounds of the general formula (I) can be prepared by process steps known per se and/or with analogous application of process steps known per se to the relevant skilled worker with knowledge of the present invention.

Each of these preferred definitions of one variable can be combined with any definitions of the remaining variables.

The inventive compounds can be in the form of racemates or of enantiopure or diastereopure compounds. The compounds may further be in non-salt form or optionally in salt form with physiologically tolerated acids or bases and may likewise be in the form of prodrugs.

Physiologically tolerated salts can be formed for example with the following anions: chloride, bromide, phosphate, carbonate, nitrate, perchlorate, sulfate, citrate, lactate, tartrate, maleate, fumarate, mandelate, benzoate, ascorbate, cinnamate, glycollate, methanesulfonate, formate, malonate, naphthalene-2-sulfonate, tosylates, salicylate and/or acetate. Further suitable acids are listed for example in "Fortschritte der Arzneimittelforschung", 1966, Birkhäuser Verlag, vol. 10, pp. 224-285.

The terms "alkyl" or "alkylene" in the meaning of the present description always comprise unbranched or branched "alkyl" or "alkylene".

$C_1$-$C_4$-Alkyl is in the meaning of the description preferably methyl, ethyl, n-propyl, i-propyl, n-butyl, sec-butyl or t-butyl.

$C_0$-Alkylene or $(CH_2)_0$ designate in the meaning of the description a single bond.

$C_1$-$C_4$-Alkylene is in the meaning of the description methylene, ethylene or branched or unbranched propylene or butylene.

$C_1$-$C_6$-Alkyl is in the meaning of the description methyl, ethyl or branched or unbranched propyl, butyl, pentyl or hexyl, preferably $C_1$-$C_4$-alkyl, i.e. methyl, ethyl, n-propyl, i-propyl, n-butyl, sec-butyl or t-butyl.

$C_1$-$C_6$-Alkylene is in the meaning of the description methylene, ethylene or branched or unbranched propylene, butylene, pentylene or hexylene, preferably $C_1$-$C_4$-alkylene, i.e. methylene, ethylene or branched or unbranched propylene or butylene.

Heteroaromatic rings are in the context of the description imidazolyl, thiazolyl, pyrrolyl, oxazolyl, isoxazolyl, 1,2,3-triazolyl, 1,2,4-triazolyl, tetrazolyl, thienyl, pyrazolyl, pyridyl, pyrazinyl, pyrimidinyl, phthalazinyl, benzimidazolyl, quinolinyl, isoquinolinyl, benzofuranyl, indolyl, benzimidazolyl, benzothiazolyl, benzothiophenyl.

Heteroaromatic mono-, bi- or tricyclic ring systems are in the context of the description imidazolyl, thiazolyl, pyrrolyl, oxazolyl, isoxazolyl, 1,2,3-triazolyl, 1,2,4-triazolyl, tetrazolyl, thienyl, pyrazolyl, pyridyl, pyrazinyl, pyrimidinyl, phthalazinyl, benzimidazolyl, quinolinyl, isoquinolinyl, benzofuranyl, indolyl, benzimidazolyl, benzothiazolyl, benzothiophenyl, carbazolyl, dibenzoazepinyl, dibenzothiophenyl, dibenzofuranyl.

The inventive compounds are effective after administration by various routes, especially orally.

The inventive compounds show good affinity for vasopressin receptors, especially the vasopressin V1b receptor subtype. Since the various vasopressin receptors mediate very different effects of vasopressin (M. Thibonnier, Exp. Opin. Invest. Drugs 1998, 7(5), 729-740; Serradeil-Le Gal, C, et al.; Prog Brain Res. 2002; 139:197-210), it is particularly important to obtain effects selectively on, for example, one vasopressin receptor, in order thus to achieve the desired effect without simultaneously causing considerable side effects. Thus, vasopressin mediates for example effects on the kidney and its function via the V2 receptor, and this would be unwanted during a possible treatment of CNS disorders. Accordingly, besides the actual affinity for the target receptor, also particularly important is the selectivity vis-à-vis the other vasopressin receptors. The inventive compounds show the advantage of having very good affinities for the vasopressin V1b receptor and simultaneously displaying an improved selectivity vis-à-vis the other receptors such as V1a, V2 and OT.

The present invention also provides the use of the inventive compounds for the treatment and/or prophylaxis of diseases in which the course of the disease is at least partially dependent on vasopressin, i.e. diseases which show an elevated vasopressin or oxytocin level which may contribute directly or indirectly to the pathological state.

The present invention further provides the use of the inventive compounds for the treatment and/or prophylaxis of diseases such as, for example, diabetes insipidus, nocturnal enuresis, incontinence, diseases in which blood coagulation disorders occur and/or for delaying micturition.

The present invention also provides the use of the inventive compounds for the treatment and/or prophylaxis of the following diseases: hypertension, pulmonary hypertension, heart failure, myocardial infarction, coronary spasm, unstable angina, PTCA (percutaneous transluminal coronary angioplasie), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness.

The inventive compounds can also be used for the treatment of various vasopressin-dependent or oxytocin-dependent complaints which have central nervous causes or causes in the HPA axis (hypothalamic pituitary adrenal axis), for example for affective disorders such as depressive disorders and bipolar disorders. These include for example dysthymic disorders, phobias, post-traumatic stress disorders, general anxiety disorders, panic disorders, seasonal depressions and sleep disorders. The disorders which can be treated according to the invention and which are associated with alterations in the HPA axis also include the disorders associated with drug withdrawal, especially withdrawal of opioid drugs or cocaine, including the increased tendency to relapse of formerly dependent individuals.

The inventive compounds can likewise be employed for treatment in cases of anxiety disorders and stress-dependent anxiety disorder such as, for example, generalized anxiety disorders, phobias, post-traumatic anxiety disorders, panic anxiety disorders, obsessive-compulsive anxiety disorders, acute stress-dependent anxiety disorders and social phobia. The inventive compounds can further be employed also for the treatment of memory impairments, Alzheimer's disease, psychoses, psychotic disorders, sleep disorders and/or Cushing's syndrome.

The compounds of the invention are further suitable for the treatment of psychotic disorders/impairments such as schizophrenia.

The compounds of the invention are further suitable for the treatment of vasomotor disorders (vasomotor symptoms VMS) such as hot flushes or night sweats, and thus also for the prophylaxis of the sequelae associated therewith, such as lack of sleep and disorders and impairments resulting therefrom.

The present invention also relates to pharmaceutical compositions which comprise an effective dose of an inventive compound or of a pharmaceutically acceptable salt thereof and suitable pharmaceutical carriers.

These pharmaceutical carriers are chosen according to the pharmaceutical form and the desired mode of administration.

The inventive compounds of the general formula I or optionally suitable salts of these compounds can be used to produce pharmaceutical compositions for oral, sublingual, subcutaneous, intramuscular, intravenous, topical, intratracheal, intranasal, transdermal or rectal administration and be administered to animals or humans in standard administration forms, mixed with conventional pharmaceutical carriers, for the prophylaxis or treatment of the above disorders or diseases.

The suitable standard administration forms comprise forms for oral administration, such as tablets, gelatin capsules, powders, granules and solutions or suspensions for oral intake, forms for sublingual, buccal, intratracheal or intranaseal administration, aerosols, implants, forms of subcutaneous, intramuscular or intravenous administration and forms of rectal administration.

The inventive compounds can be used in creams, ointments or lotions for topical administration.

In order to achieve the desired prophylactic or therapeutic effect, the dose of the active basic ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose may be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets can be coated with sucrose, a cellulose derivative or another suitable substance, or be treated otherwise in order to display a sustained or delayed activity and in order to release a predetermined amount of the active basic ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable color.

Water-dispersible powders or granules may comprise the active ingredients mixed with dispersants, wetting agents or suspending agents, such as polyvinylpyrrolidones, and sweeteners or masking flavors.

Rectal administration is achieved by using suppositories which are prepared with binders which melt at the rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active basic ingredient may also be formulated as microcapsules or centrosomes, where suitable with one or more carriers or additives.

In addition to the compounds of the general formula (I) or their pharmaceutically acceptable salts, the inventive compositions may comprise other active basic ingredients which may be beneficial for the treatment of the disorders or diseases indicated above.

The present invention thus further relates to pharmaceutical compositions in which a plurality of active basic ingredients are present together, at least one of these being an inventive compound of the general formula I.

The inventive compounds of the general formula I represent antagonists of the so-called receptors of the vasopressin/oxytocin family. Such compounds can be investigated in suitable assays which ascertain the affinity for a receptor, where the affinity constant $K_i$ represents a measure of the potency of the compounds and a smaller value represents a greater potency.

The inventive compounds of the general formula I have been tested for example for their receptor affinity for vasopressin receptors such as V1a and V1b, and for their effect as antagonists of the effect mediated by vasopressin in a cellular assay. The inventive compounds of the general formula I show surprisingly good effects therein.

Thus, Examples 1, 2, 3, 4, 5, 6, 7, 10, 11 and 12 have shown good and very good affinities for the vasopressin V1b receptor, and their Ki values are below 100 nM. In addition, some of these compounds show good selectivity vis-à-vis the other receptors of the vasopressin/oxytocin V1a, V2 and OT receptor family. This improved selectivity is regarded as important because appreciable binding to these receptors distinctly increases the risk of unwanted side effects.

The assays can be carried out for the inventive compounds for example in accordance with the assay procedures below.

Vasopressin V1a Receptor Binding Assay

The substances were dissolved in a concentration of $10^{-2}$ M in dimethyl sulfoxide (DMSO) and further diluted to $10^{-3}$ M to $10^{-9}$ M in DMSO. These DMSO solutions are diluted 1:10 with assay buffer. The substance concentration was further diluted 1:10 in the assay mixture.

The binding assay was carried out by a method based on that of Tahara et al. (Tahara A et al., Brit. J. Pharmacol. 125, 1463-1470 (1998)). In the assay mixture (0.250 ml), membranes (50 µg of protein in incubation buffer (50 mM Tris, 10 mM $MgCl_2$, 0.1% BSA, adjusted to pH 7.4 with HCl)) from CHO cells with stably expressed human V1a receptors (preparation V1a clone 5.0, with protease inhibitors, Roche complete Mini # 1836170) were incubated with 0.04 nM $^{125}$iodine-AVP (NEX128) in incubation buffer (total binding) or additionally with increasing concentrations of test substance (displacement experiment). The nonspecific binding was determined with $10^{-6}$ M AVP. Determinations in triplicate were carried out.

After incubation at room temperature for 60 minutes, the free radioligand was filtered off by vacuum filtration (Skatron cell harvester 7000) through Whatman GF/B glass fiber filter mats, and the filters were transferred into scintillation vials. The liquid scintillation measurement took place in a model 2000 or 2200CA Tricarb instrument (Packard). Conversion of the measured cpm into dpm was carried out with the aid of a standard quench series.

The binding parameters were calculated by nonlinear regression in SAS. The algorithms of the program operate in analogy to the LIGAND analysis program (Munson P J and Rodbard D, Analytical Biochem. 107, 220-239 (1980)).

The affinities for the human vasopressin V1a receptor were measured, and affinity constants determined, in the above assay for the inventive examples.

Vasopressin V1b Receptor Binding Assay:

The substances were dissolved in a concentration of $10^{-2}$ M in DMSO and further diluted to $10^{-3}$ M to $10^{-9}$ M in DMSO. This DMSO predilution series was diluted 1:10 with assay buffer. The substance concentration was further diluted 1:10 in the assay mixture.

The binding assay was carried out by a method based on that of Tahara et al. (Tahara A et al., Brit. J. Pharmacol. 125, 1463-1470 (1998)). In the assay mixture (0.250 ml), membranes (58 µg of protein in incubation buffer) from CHO—K1 cells with stably expressed human V1b receptors (preparation V1b-3H2, with protease inhibitors, Roche complete Mini # 1836170) were incubated with 1.5 nM $^3$H-AVP (8-Arg-vasopressin, NET 800) in incubation buffer (50 mM Tris, 10 mM $MgCl_2$, 0.1% BSA, adjusted to pH 7.4 with HCl) (total binding) or additionally with increasing concentrations of test substance (displacement experiment). The nonspecific binding was determined with $10^{-6}$ M AVP. Determinations in triplicate were carried out.

Incubation buffer: 50 mM Tris, 10 mM $MgCl_2$, 0.1% BSA, adjusted to pH 7.4 with HCl.

After incubation at room temperature for 60 minutes, the free radioligand was filtered off by vacuum filtration (Skatron cell harvester 7000) through Whatman GF/B glass fiber filter mats, and the filters were transferred into scintillation vials. The liquid scintillation measurement took place in a model 2000 or 2200CA Tricarb instrument (Packard). Conversion of the measured cpm into dpm was carried out with the aid of a standard quench series.

The binding parameters were calculated by nonlinear regression in SAS. The algorithms of the program operate in analogy to the LIGAND analysis program (Munson P J and Rodbard D, Analytical Biochem. 107, 220-239 (1980)).

The affinities for the human vasopressin V1b receptor were measured, and affinity constants determined, in the above assay for the inventive examples.

Vasopressin V2 Receptor Binding Assay:

Substances:

The test substances were dissolved in a concentration of $10^{-2}$ M in DMSO. The further dilution of these DMSO solutions took place in incubation buffer (50 mM Tris, 10 mM $MgCl_2$, 0.1% BSA, pH 7.4).

Membrane Preparation:

CHO—K1 cells with stably expressed human vasopressin V2 receptor (clone 23) were harvested and homogenized in 50 mM Tris-HCl and in the presence of protease inhibitors (Roche complete Mini # 1836170) with a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)). Incubation buffer was: 50 mM Tris, 10 mM $MgCl_2$, 0.1% BSA, pH 7.4.

In assay mixture (250 µl), membranes (50 µg/ml protein in incubation buffer) from CHO—K1 cells with stably expressed human V2 receptors (cell line hV2_23_CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem # H1780). Determinations were carried out in triplicate.

After incubation at room temperature for 60 minutes, the free radioligand was filtered off by vacuum filtration (Skatron cell harvester 7000) through Whatman GF/B glass fiber filter mats, and the filters were transferred into scintillation vials. The liquid scintillation measurement took place in a model 2000 or 2200CA Tricarb instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki.

Oxytocin Receptor Binding Assay

The substances were dissolved in a concentration of $10^{-2}$ M or $10^{-3}$ M in DMSO and diluted with incubation buffer (50 mM Tris, 10 mM $MgCl_2$, 0.1% BSA, pH 7.4).

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. The lyzed cells were then centrifuged at 750×g at 4° C. for 20 minutes, the residue was taken up in incubation buffer, and aliquots of $10^7$ cells/ml were prepared. The aliquots were frozen at −80° C. until used.

On the day of the experiment, the cells were thawed, diluted with incubation buffer and homogenized using a Multipette Combitip (Eppendorf, Hamburg). The reaction mixture of 0.250 ml was composed of 2 to $5 \times 10^4$ recombinant cells, 3-4 nM $^3H$-oxytocin (Perkin Elmer, NET 858) in the presence of test substance (inhibition plot) or only incubation buffer (total binding). The nonspecific binding was determined with $10^{-6}$ M oxytocin (Bachem AG, H2510). Determinations in triplicate were set up. Bound and free radioligand were separated by filtration under vacuum with Whatman GF/B glass fiber filters using a Skatron cell harvester 7000. The bound radioactivity was determined by liquid scintillation measurement in a Tricarb beta counter, model 2000 or 2200CA (Packard).

The binding parameters were calculated by nonlinear regression analysis (SAS), in analogy to the LIGAND program of Munson and Rodbard (Analytical Biochem 1980; 107: 220-239). The Kd of $^3H$-oxytocin for the recombinant hOT receptors is 7.6 nM and was to determine the Ki.

Effect on Vasopressin-Induced Calcium Increase in Cells Having a Cloned Human Vasopressin Receptor The functional activity of the test substances was investigated on CHO—K1 cells which were stably transfected with the human V1b receptor. 50 000 cells were seeded in each well of a microtiter plate with 96 wells and incubated in culture medium in a saturated water vapor atmosphere with 5% $CO_2$ at 37° C. overnight. The culture medium consisted of DMEM/Nut Mix F12 with Glutamax I (from Invitrogen), 10% fetal calf serum, 100 units/ml penicillin, 100 μg/ml streptomycin and 800 μg/ml Geneticin. The following day, the cells were washed with culture medium and loaded with a fluorescent dye for calcium in accordance with the manufacturer's statements ($Ca^{++}$-Plus-Assay Kit, Molecular Devices). The cells were loaded in the presence of probenecid (1 vol %). The test substances were diluted with culture medium (final concentration $10^{-10}$ to $10^{-5}$M) and incubated with the dye-loaded cells at room temperature for 15 minutes. The Arg-vasopressin ($10^{-8}$M) was added and the maximum fluorescence signal was determined using a FLIPR-96 measuring instrument (Molecular Devices). Concentration-effect plots were constructed using nonlinear regression algorithms (GraphPad Prism 3.0). Kb values were calculated from IC50 values by the method of Cheng and Prusoff (Kb=IC50/1+L/EC50).

The affinities of the compounds (I) of the invention for the human vasopressin V1b receptor were measured in accordance with the above assays, and the affinity constants. (Ki) were determined. Table 1 below details the V1b receptor affinity of selected compounds (++ means <50 nM and + means 50-500 nM).

TABLE 1

| Example | V1b Ki |
|---------|--------|
| 1 | ++ |
| 2 | ++ |
| 3 | ++ |
| 4 | ++ |
| 5 | ++ |
| 6 | ++ |
| 7 | + |
| 8 | + |
| 10 | + |
| 11 | ++ |
| 12 | ++ |

Examples of synthetic routes for preparing the inventive compounds are described below.

The inventive oxindoles can be prepared in various ways as outlined in synthesis schemes 1-4. The variables in these synthesis schemes have the same meanings as in the general formula (I).

SYNTHESIS SCHEME 1

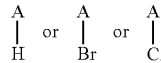

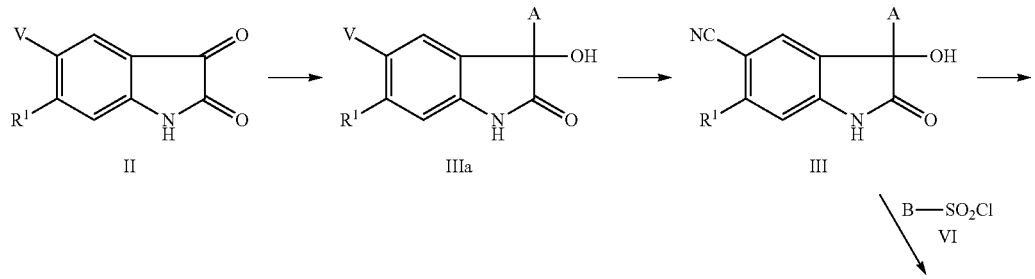

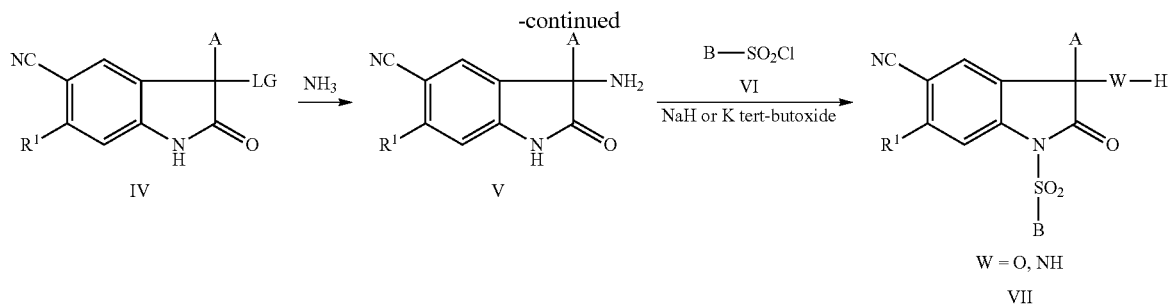

V = G or CN
G = I, Br
M = MgBr, MgCl or Li
LG = leaving group

Starting from aromatic compounds A-H or A-Br or A-Cl (A=,

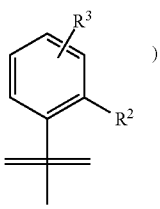

)

which are metallated in a conventional way with the formation of A-M (IX), such as, for example, as Grignard compound or organolithium compound, it is possible to obtain the 3-hydroxyoxindoles IIIa by addition IX onto isatins II. The metallated compounds IX can be obtained in a conventional way from halo- or hydrocarbon compounds. Exemplary methods are present in Houben-Weil, Methoden zur Organischen Chemie, vol. 13, 1-2, chap. Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IIIa bear a CN, Br or I in position 5. In the case of Br and I, these radicals can be converted into the 5-cyano-3-hydroxyoxindoles III with KCN and with Pd(0) catalysis in solvents such as dimethylformamide (DMF) with the addition of bases such as $K_2CO_3$ or other carbonates and amines at elevated temperature. The Pd(0) salts which can be used are for example transition metal complexes which are prepared in situ from $PdCl_2$ or $PdOAc_2$ by adding phosphines such as tris(orthotolyl)phosphine. It is likewise possible to employ commercial palladium complexes or phosphine ligands. It is also possible to carry out the introduction of cyanide later in the synthetic sequence, for example on the compounds V, VII or else I, if I or Br is present there instead of the CN in position 5 on the oxindole.

The 3-hydroxyoxindoles III can be converted into the compounds IV which have a leaving group LG in position 3, it being possible for the leaving group LG to be a conventional leaving group such as, for example, halide, mesylate or tosylate. Thus, for example (LG=chlorine), the intermediate IV can be prepared by treating the alcohol III with thionyl chloride in the presence of a base such as, for example, pyridine. Alternatively, alcohols III can be converted into the mesylate IV using methanesulfonyl chloride in the presence of a base such as, for example, triethylamine. The compounds IV are subsequently reacted with aqueous ammonia, resulting in the amines V. For example, such substitution reactions with amine in the presence of a base such as N,N-diisopropylethylamine can result in the analogous 3-aminooxindoles V. After deprotonation with a strong base such as, for example, potassium tert-butoxide or sodium hydride in DMF, V can subsequently be converted by treatment with sulfonyl chlorides VI into the compound VII. The corresponding derivatives VII with W=O can be obtained in an analogous manner starting from the alcohols III.

SYNTHESIS SCHEME 2

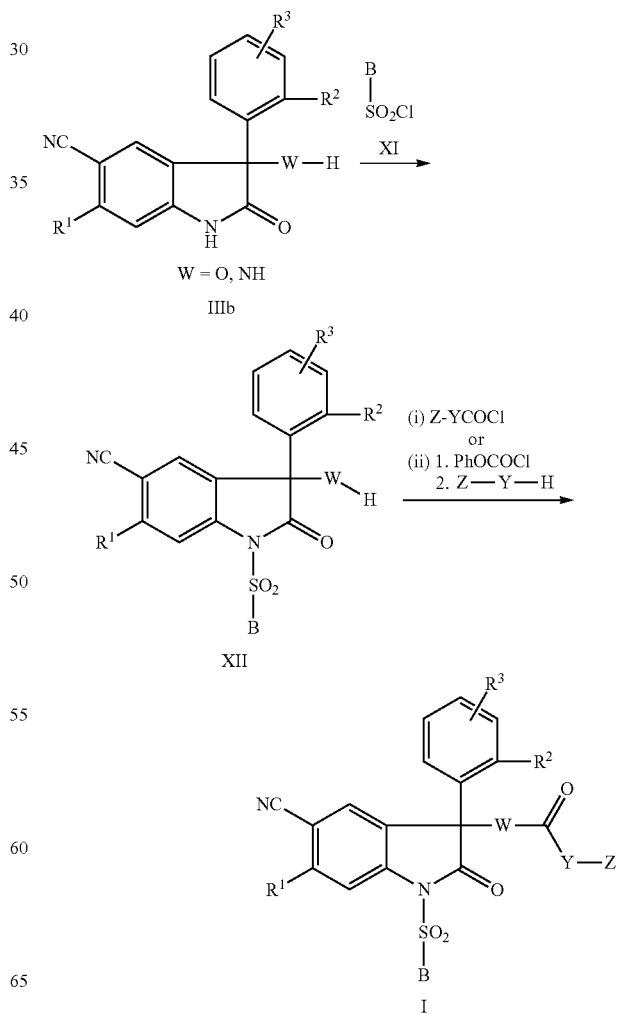

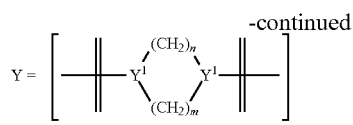

The inventive compounds I are prepared by initially reacting the oxindoles IIIb with sulfonyl chlorides XI under the conditions already described above. The sulfonyl chlorides XI employed can either be acquired by purchase or be prepared in an analogous manner to known processes (see, for example, J. Med. Chem. 40, 1149 (1997)). The inventive compounds I are prepared in various ways starting from the sulfonylated compounds XII: Suitable routes are for example (i) reaction with carbamoyl chlorides Z-Y—CO—Cl in the presence of a base such as, for example, triethylamine; (ii) activation with phenyl chloroformate in the presence of a base such as, for example, pyridine and subsequent reaction with amines Z-Y—H, if appropriate at elevated temperatures. The amines Z-Y—H can however be acquired by purchase or be prepared by methods known from the literature.

Inventive compounds I which have a functionalized nitrogen atom in position 3 (e.g. amides, sulfonamides, carbamates and ureas) are prepared in analogy to synthesis scheme 2: the 3-aminooxindoles XII (W=NH) are converted by reaction with reagents for derivatizing amino groups, such as, for example, carboxylic acids, carbonyl chlorides, carboxylic anhydrides, sulfonyl chlorides, chloroformates, isocyanates or carbamoyl chlorides, into the inventive compounds I, generally making use of conventional methods (see J. March, Advanced Organic Chemistry, 1992, 4th edition, Wiley, New York, p. 417-421; 499; 903). It is additionally possible for the 3-amino group in the compounds XII (W=NH) to be substituted by treatment with alkylating agents such as, for example, alkyl bromides, iodides or mesylates, and by reaction with aldehydes or ketones in the presence of reducing agents such as, for example, sodium cyanoborohydride, in the manner of a reductive amination (J. March, Advanced Organic Chemistry, 1992, 4th edition, Wiley, New York, p. 411; 898).

Alternatively, the building blocks XII can be prepared by the two-stage process shown in the synthesis scheme 3.

SYNTHESIS SCHEME 3

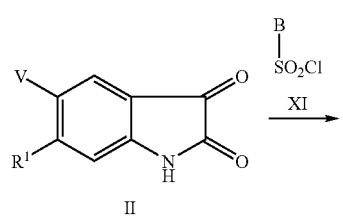

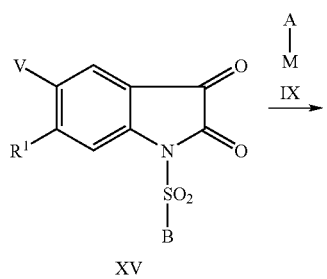

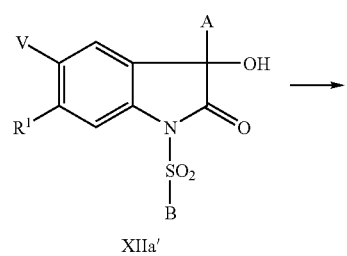

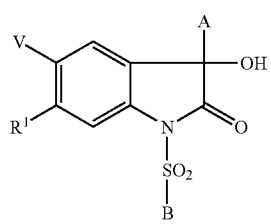

V = G or CN
M = MgBr, MgCl or Li

Sulfonylated isatins XV are obtained by deprotonation of isatins II with a strong base such as, for example, sodium hydride or potassium tert-butanolate, and subsequent treatment with sulfonyl chlorides XI. The compounds XIIa' are obtained in the second step of synthesis scheme 3 by addition of metallated compounds IX onto the 3-keto group of the sulfonylisatins XV. Introduction of cyanide with KCN is possible in analogy to synthesis scheme 1 to give the product XIIa. The methods are analogous to the processes described above.

SYNTHESIS SCHEME 4

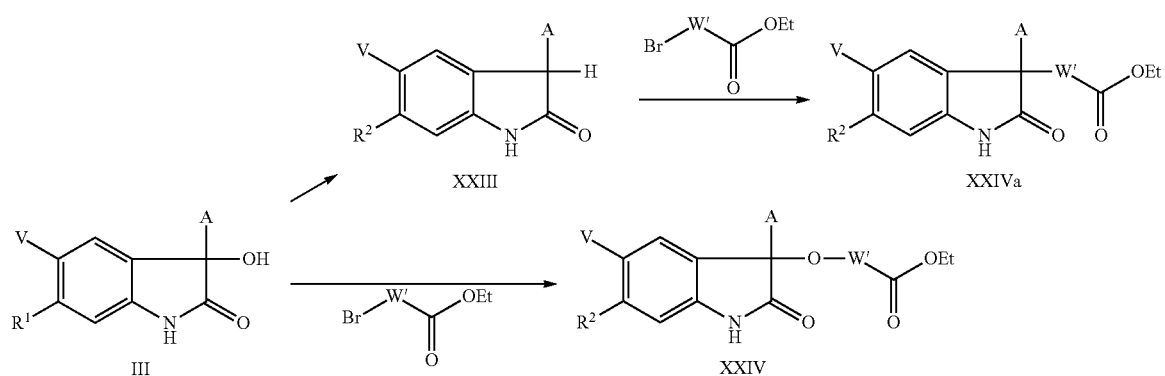

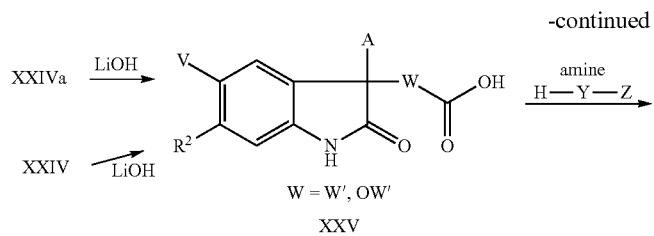
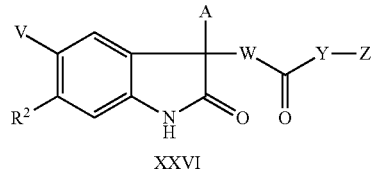

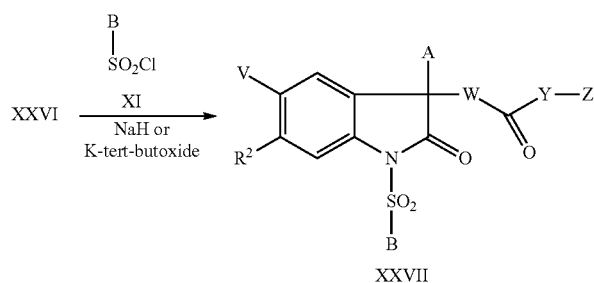

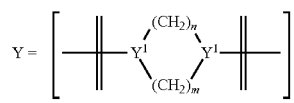

Et = C₂H₅
V = G or CN
W' = CH₂

Routes to compounds in which W can be varied are outlined in synthesis scheme 4. Alcohols III are reacted with halo carboxylic esters to give the derivatives XXIV, preferably using bromo carboxylic esters and chloro carboxylic esters, although analogous mesylates or tosylates and similar compounds in which a leaving group is present can be used. The reactions can be carried out for example in polar solvents such as DMF or tetrahydrofuran (THF), with the addition of basic substances such as, for example, NaH, potassium tert-butanolate, sodium ethanolate, trialkylamines or potassium carbonate. The reactions can be carried out at room temperature or elevated temperatures such as the boiling point of the solvent. Reaction of the indol-2-one XXIII to give XXIV is carried out analogously, the compounds XXIVa being obtained. The indolones XXIII can be prepared synthetically either from the analogous alcohols III by reducing the alcohol group, for example with triethylsilane or in analogy to Mullock, E. B. et al., J. Chem. Soc. C, 1970, 6, 829-833, Ghosal, S. et al., Ind. J. Chem., 1969m 7, 1095-1097 and U.S. Pat. No. 2,759,935. The esters XXIV or XXIVa can be converted with acids such as HCl and $H_2SO_4$ or bases such as NaOH, KOH or LiOH into the carboxylic acids XXV, normally operating in solvents such as alcohols or THF, with the addition of aqueous acids or bases at room temperature or temperatures of 25-70° C. The carboxylic acids XXV can be converted into the derivatives XXVI by reacting the carboxylic acids with, for example, amines by using conventional coupling conditions as detailed for example in R. C. Larock, Comprehensive Organic Transformations, Wiley 1999, Chap. 9. Introduction of the sulfonic acid residue B—$SO_2$— takes place in a manner analogous to that described above. As alternative to scheme 4, the last two steps can also be carried out in the reverse order.

EXPERIMENTAL SECTION

Example 1

5-Cyano-3-(2-ethoxyphenyl)-2-oxo-1-(quinoline-8-sulfonyl)-2,3-dihydro-1H-indol-3-yl 4-(thiazol-2-yl)piperazine-1-carboxylate 1a) 3-(2-Ethoxyphenyl)-3-hydroxy-5-iodoindol-2-one 4 g (164 mMol) of magnesium turnings and 5% of the total amount of 2-bromo-1-ethoxybenzene were put into 20 ml of ether and, after addition of a little iodine, were heated until the reaction started. 33.1 g (165 mMol) of 2-bromo-1-ethoxybenzene dissolved in 100 ml of ether were slowly added dropwise to the boiling solution in such a way that the reaction continued with gentle boiling. Then, while cooling slightly to 20° C., 15 g (54.9 mMol) of 5-iodoisatin in 400 ml of anhydrous tetrahydrofuran were added dropwise. The mixture was then stirred at room temperature for 2 h. The reaction solution was poured into an aqueous $NH_4Cl$ solution with stirring. This aqueous phase was extracted several times with ethyl acetate, and the combined aqueous phase was washed four times with water, dried and concentrated in vacuo, resulting in the product as a crystalline precipitate. 19.2 g of the product were obtained.

1b) 5-Cyano-3-(2-ethoxyphenyl)-3-hydroxy-indol-2-one 37.2 g (94 mMol) of the product 1a and 11.1 g (94 mMol) of zinc cyanide in 300 ml of DMF were heated to 95° C. Then 1.6 g (1.38 mMol) of tetrakis-(triphenylphosphine)palladium (0) were added in portions every 10 minutes. After 45 minutes, the reaction mixture was poured into ice-water and extracted with ethyl acetate. The organic phase was washed with saturated NaCl solution, dried and concentrated in vacuo. The residue obtained in this way crystallizes from a little ethyl acetate. 24 g of the product were obtained.

1c) 3-(2-Ethoxyphenyl)-3-hydroxy-2-oxo-1-(quinoline-8-sulfonyl)-2,3-dihydro-1H-indole-5-carbonitrile 2.3 g (10.6 mMol) of potassium tert-butanolate are added to 5.5 g (18.7 mMol) of the intermediate 1b in 40 ml of DMF at 0° C. The reaction mixture was stirred for 1 h. Then 4.25 g (18.7 mMol) of 8-quinolinesulfonyl chloride were added at 0° C. The reaction solution was stirred at 0° C. for three hours and then at room temperature for 16 h. This reaction solution was poured into aqueous $K_2CO_3$ solution, resulting in a precipitate which was isolated. This solid was dissolved in methylene chloride, dried and concentrated in vacuo. The resulting residue was recrystallized from ethanol. 6.2 g of the product were obtained.

1d) 5-Cyano-3-(2-ethoxyphenyl)-2-oxo-1-(quinoline-8-sulfonyl)-2,3-dihydro-1H-indol-3-yl 4-(thiazol-2-yl)piperazine-1-carboxylate 3.4 g (21.6 mMol) of ethyl chloroformate were added dropwise to 3 g (6.2 mMol) of intermediate 1c in 30 ml of pyridine at 0° C. The mixture was stirred for a further 1 h. The reaction solution was then poured into aqueous $K_2CO_3$ solution, and the resulting precipitate was isolated. This precipitate was dissolved in methylene chloride, dried and concentrated in vacuo. The resulting residue was then crystallized from ether. 3.3 g of a solid were obtained. 112 mg of 4(1-thiazol-2-yl)piperazine were added to 100 mg of this solid in 5 ml of THF, and the mixture was stirred at room temperature for 16 h. The mixture was then heated at reflux for 4 h. The solvent was removed in vacuo. The resulting residue was recrystallized from methanol. 80 mg of the product were obtained.

$^1$H-NMR (CDCl$_3$): δ=1.25(3H), 2.75(2H), 3.1(1H), 3.25 (1H), 3.4(2H), 3.6(2H), 3.8(1H), 4.05(1H), 6.6(1H), 6.8(1H), 6.95(1H), 7.15-7.35(3H), 7.4(1H), 7.6(1H), 7.65(1H), 7.75 (1H), 8.1(1H), 8.15(1H), 8.55(1H), 8.65(1H) and 8.75(1H) ppm.

Example 2

4-(Pyridin-4-yl)piperazin-1-[5-cyano-3-(2-ethoxyphenyl)-2-oxo-1-(quinoline-8-sulfonyl)-2,3-dihydro-1H-indol-3-yl]carboxamide

2a) 3-Amino-5-cyano-3-(2-ethoxyphenyl)indol-2-one 8.0 g (27.2 mMol) of intermediate 1b and 43 ml (54.4 mMol) of pyridine were dissolved in 70 ml of methylene chloride. Then, at 0° C., 3 ml (40.8 mMol) of SOCl$_2$ were slowly added dropwise. The reaction mixture was then stirred for a further 30 minutes. The reaction solution was subsequently poured into ice-water, and the organic phase was separated off, washed with water, dried and concentrated in vacuo. This residue was added at 0° C. to a solution of 300 ml of 0.5M NH$_3$ solution in dioxane and 150 ml of methylene chloride. The mixture was stirred at room temperature for 16 h. The reaction solution was concentrated in vacuo, and the residue obtained in this way was suspended in water. The precipitate was separated off and recrystallized from a little methanol. 4.7 g of the product were obtained.

2b) Phenyl [5-cyano-3-(2-ethoxyphenyl)-2-oxo-2,3-dihydro-1H-indol-3-yl]-carbamate 1.2 ml (9.38 mMol) of phenyl chloroformate were added dropwise to 2.5 g (8.5 mMol) of product 2a dissolved in 50 ml of pyridine at 0° C. The reaction solution was then stirred at room temperature for 16 h. The solution was subsequently poured into ice-water, and the aqueous phase was extracted with ethyl acetate (AcOEt). The organic phase was washed several times with water, dried and concentrated in vacuo. 3.9 g of the product were obtained.

2c) 4-Pyridin-4-ylpiperazine-1-[5-cyano-3-(2-ethoxyphenyl)-2-oxo-2,3-dihydro-1H-indol-3-yl]carboxamide 4 g (8.5 mMol) of intermediate 2b and 5.6 g (34.1 mMol) of 1-(4-pyridyl)-piperazine in 70 ml of tetrahydrofuran were stirred at room temperature for 16 h. The solvent was then removed in vacuo. The residue was partitioned between water and ethyl acetate. The aqueous phase was washed twice with ethyl acetate. The combined ethyl acetate phases were again washed with water, dried and concentrated in vacuo. The residue was dissolved in a little ethanol, and this solution was added dropwise to ether, resulting in a solid which was isolated. 1.9 g of the product were obtained.

2d) 4-(Pyridin-4-yl)piperazine-1-[5-cyano-3-(2-ethoxyphenyl)-2-oxo-1-(quinoline-8-sulfonyl)-2,3-dihydro-1H-indol-3-yl]carboxamide 51 mg (0.46 mMol) of potassium tert-butanolate were added in portions to 200 mg (0.41 mMol) of intermediate 2c in 4 ml of anhydrous dimethylformamide at 0° C., and the mixture was stirred for about 60 minutes. Subsequently, 104 mg (0.46 mMol) of 8-quinolinesulfonyl chloride were added at 0° C. The mixture was stirred at room temperature for 16 h. The reaction solution was then poured into 1M NaOH, resulting in a precipitate which was isolated. This precipitate was purified by chromatography on silica gel (eluent: CH$_2$Cl$_2$/ CH$_3$OH=9/1). The product obtained in this way was crystallized from CH$_2$Cl$_2$/ether. 68 mg of the product were obtained.

$^1$H-NMR (CDCl$_3$): δ=1.5(3H), 3.2-3.4(8H), 4.1-4.3(2H), 6.5(1H), 6.6(2H), 6.9(2H), 7.15(1H), 7.4(1H), 7.6(1H), 7.7 (2H), 8.1(1H), 8.2(1H), 8.25(2H), 8.4(1H), 8.55(1H) and 8.75(1H) ppm.

The following compounds were prepared in an analogous manner to examples 1 and 2 using methodological processes analogous to the described methods:

Example 3

4-(Pyridin-4-yl)piperazin-1-[5-cyano-3-(2-ethoxyphenyl)-2-oxo-1-(thien-3-yl-sulfonyl)-2,3-dihydro-1H-indol-3-yl]carboxamide $^1$H-NMR (CDCl$_3$): δ=1.5(3H), 3.3-3.6(8H), 4.15(1H), 4.25(1H), 6.6(2H), 6.65(1H), 6.95(2H), 7.05(1H), 7.3(1H), 7.35(1H), 7.5-7.7(3H), 8.0(1H), 8.3(2H) and 8.35(1H) ppm.

Example 4

5-Cyano-3-(2-ethoxyphenyl)-2-oxo-1-(thien-3-ylsulfonyl)-2,3-dihydro-1H-indol-3-yl 4-(pyridin-4-yl)piperazine-1-carboxylate $^1$H-NMR (CDCl$_3$): δ=1.2(3H), 3.15-3.35(4H), 3.35-3.5(2H), 3.75-3.9(3H), 4.0(1H), 6.65(2H), 6.8(1H), 7.05(1H), 7.25(1H), 7.35(2H), 7.55(1H), 7.65(1H), 7.7(1H), 8.05(1H) and 8.3(3H) ppm.

Example 5

5-Cyano-3-(2-ethoxyphenyl)-2-oxo-1-(quinoline-8-sulfonyl)-2,3-dihydro-1H-indol-3-yl 4-(pyridin-2-yl)piperazine-1-carboxylate $^1$H-NMR (CDCl$_3$): δ=1.25(3H), 2.75(2H), 3.2-3.4(2H), 3.5(2H), 3.6(2H), 3.8(1H), 4.05(1H), 6.6(1H), 6.65(1H), 6.8(1H), 6.95(1H) 7.0(1H), 7.2-7.35(2H), 7.4(1H), 7.5(1H), 7.6-7.7(2H), 7.75(1H), 8.1(1H), 8.15(2H), 8.55(1H), 8.7(1H) and 8.75(1H) ppm.

Example 6

5-Cyano-3-(2-ethoxyphenyl)-2-oxo-1-(quinoline-8-sulfonyl)-2,3-dihydro-1H-indol-3-yl 4-(pyrimidin-2-yl)piperazine-1-carboxylate $^1$H-NMR (CDCl$_3$): δ=1.25(3H), 2.65(2H), 3.5(4H), 3.7-3.9(3H), 4.05(1H), 6.5(1H), 6.8(1H), 7.0(1H), 7.2-7.35(2H), 7.4(1H), 7.6(1H), 7.65(1H), 7.7(1H), 7.85(1H), 8.1(3H), 8.2(1H), 8.3(2H), 8.55(1H), 8.65(1H) and 8.75(1H) ppm.

Example 7

5-Cyano-3-(2-ethoxyphenyl)-2-oxo-1-(quinoline-8-sulfonyl)-2,3-dihydro-1H-indol-3-yl 4-(pyrazin-2-yl)piperazine-1-carboxylate $^1$H-NMR (CDCl$_3$): δ=1.2(3H), 2.75(2H), 3.25(1H), 3.35(1H), 3.6(4H), 3.8(1H), 4.05(1H), 6.8(1H), 7.0(1H), 7.2-7.35(2H), 7.4(1H), 7.6(1H), 7.65(1H), 7.75(1H), 7.85(1H), 8.1(3H), 8.2(1H), 8.65(1H), 8.7(1H) and 8.75(1H) ppm.

Example 8

5-Cyano-3-(2-ethoxyphenyl)-2-oxo-1-(thien-3-ylsulfonyl)-2,3-dihydro-1H-indol-3-yl 4-(thiazol-2-yl)piperazine-1-carboxylate $^1$H-NMR (CDCl$_3$): δ=1.25(3H), 3.2(3H), 3.4(2H), 3.55(2H), 3.7-3.9(3H), 4.05(1H), 6.6(1H), 6.8(1H), 7.05(1H), 7.2(1H), 7.25(1H), 7.3(1H), 7.35(2H), 7.55(1H), 7.65(1H), 7.7(1H), 8.05(1H) and 8.35(1H) ppm.

Example 9

5-Cyano-3-(2-ethoxyphenyl)-2-oxo-1-(thien-3-ylsulfonyl)-2,3-dihydro-1H-indol-3-yl 4-(5-cyanopyridin-2-yl)piperazine-1-carboxylate $^1$H-NMR (CDCl$_3$): δ=1.2(3H), 3.25(2H), 3.6(2H), 3.7-3.9(5H), 4.0(1H), 6.55(1H), 6.8(1H), 7.05(1H), 7.25(1H), 7.35(2H), 7.55(1H), 7.65(2H), 7.7(1H), 8.05(1H), 8.3(1H) and 8.4(1H) ppm.

Example 10

4-(5-Cyanopyridin-2-yl)piperazine-1-[5-cyano-3-(2-ethoxyphenyl)-2-oxo-1-(thien-3-ylsulfonyl)-2,3-dihydro-1H-indol-3-yl]carboxamide $^1$H-NMR (CDCl$_3$): δ=1.3(3H), 3.4(4H), 3.7(4H), 4.15(1H), 4.2(1H), 6.55(1H), 6.65(1H), 6.95(2H), 7.05(1H), 7.3(1H), 7.4(1H), 7.5-7.75(4H) 8.35(1H) and 8.4(1H) ppm.

Example 11

5-Cyano-3-(2-ethoxyphenyl)-2-oxo-1-(quinoline-8-sulfonyl)-2,3-dihydro-1H-indol-3-yl 4-(5-cyanopyridin-2-yl)piperazine-1-carboxylate $^1$H-NMR (CDCl$_3$): δ=1.2(3H), 2.75(2H), 3.35(1H), 3.5(1H), 3.5-3.7(4H), 3.8(1H), 4.05(1H), 6.5(1H), 6.8(1H), 6.95(1H), 7.2(1H), 7.3(1H), 7.4(1H), 7.5-7.7(3H), 7.75(1H), 8.1(1H), 8.15(1H), 8.4(1H), 8.55(1H), 8.7(1H) and 8.75(1H) ppm.

Example 12

5-Cyano-3-(2-ethoxyphenyl)-2-oxo-1-(quinoline-8-sulfonyl)-2,3-dihydro-1H-indol-3-yl 4-(pyridin-4-yl)piperazine-1-carboxylate $^1$H-NMR (CDCl$_3$): δ=1.25(3H), 2.7(2H), 2.95-3.2(2H), 3.3(2H), 3.6(2H), 3.8(1H), 4.05(1H), 6.55(1H), 6.8(1H), 6.95(1H), 7.2-7.4(2H), 7.45(1H), 7.6(1H), 7.65(1H), 7.75(1H), 8.1(1H), 8.2(1H), 8.2(2H), 8.55(1H), 8.7(1H) and 8.75(1H) ppm.

We claim:
1. A compound of the formula (I):

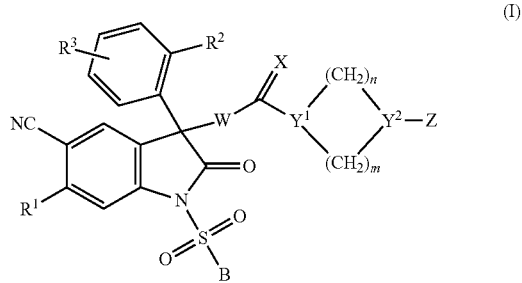

in which
R$^1$ is hydrogen, C$_1$-C$_4$-alkyl, O—(C$_1$-C$_4$-alkyl), Cl or F;
R$^2$ is O—C$_1$-C$_4$-alkyl, C$_1$-C$_6$-alkyl, or Cl;
R$^3$ is hydrogen, F, Cl, (CH$_2$)$_{0-2}$—CN, CF$_3$, OCF$_3$, CONH$_2$, CONH(C$_1$-C$_4$-alkyl), CON(C$_1$-C$_4$-alkyl)(C$_1$-C$_4$-alkyl), NHCHO, NHCONH$_2$, NH(C$_0$-C$_4$-alkylene)CONH$_2$, NH(C$_0$-C$_4$-alkylene)CONH(C$_1$-C$_4$-alkyl), NHCOCH$_3$, NO$_2$, (CH$_2$)$_{1-2}$—OH, O—C$_1$-C$_6$-alkyl, (CH$_2$)$_{1-2}$—O—C$_1$-C$_4$-alkyl, O—C$_0$-C$_4$-alkylene-phenyl, phenyl, C$_1$-C$_6$-alkyl, C$_2$-C$_6$-alkenyl or C$_2$-C$_6$-alkynyl;
B is a cyclic radical selected from the group consisting of the quinolinyl, thienyl, pyridinyl and pyrimidinyl radicals, which may each be substituted by the radicals R$^4$ and R$^5$, where R$^4$ and R$^5$ are selected independently of one another from the group consisting of hydrogen, F, Cl, CN, NO$_2$, O—C$_1$-C$_4$-alkyl and C$_1$-C$_6$-alkyl;

where
B may additionally be substituted by one, two, three or four radicals selected from the group consisting of $R^4$, $R^5$, $R^6$ and $R^7$, where $R^4$, $R^5$, $R^6$ and $R^7$ are independently of one another and independently of their respective occurrence be selected from the group consisting of hydrogen, Cl, Br, I, F, $(CH_2)_{0-2}$—CN, $CF_3$, $OCF_3$, $CONH_2$, $CONH(C_1\text{-}C_4\text{-alkyl})$, $CON(C_1\text{-}C_4\text{-alkyl})(C_1\text{-}C_4\text{-alkyl})$, NHCHO, $NH(C_0\text{-4-alkylene})CONH(C_1\text{-}C_4\text{-alkyl})$, $NHCOCH_3$, $NO_2$, OH, O—$C_1\text{-}C_4$-alkyl, $(CH_2)_{0-2}$—O—$(CH_2)_{0-3}$—$CH_3$, O—CO—$C_4$-alkylene-phenyl, phenyl, $C_1\text{-}C_6$-alkyl, $C_2\text{-}C_6$-alkenyl and $C_2\text{-}C_6$-alkynyl;
W is O, $CH_2$ or NH;
X is O, NH or N—CN; and
$Y^1$ is N;
$Y^2$ is N;
m is 2;
n is 2;
Z is a radical selected from the group consisting of

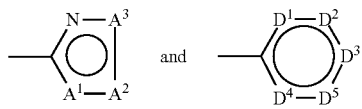

where
$A^2$ and $A^3$ independently of one another are N or C;
$A^1$ is N, C, O or S;
$D^1$, $D^2$, $D^3$, $D^4$ and $D^5$ independently of one another are C or N, but where at least one of the variables $D^1$, $D^2$, $D^3$, $D^4$ or $D^5$ is N,
and where
Z may in each case be substituted by the radicals $R^8$, $R^9$ and $R^{10}$, where $R^8$, $R^9$ and $R^{10}$ independently of one another have the following meanings, namely
$R^8$ is hydrogen, Cl, F, CN, $CF_3$, $OCF_3$, $CONH_2$, $NHCOCH_3$, $NO_2$, OH, OC—$C_1\text{-}C_4$-alkyl, $C_1\text{-}C_4$-alkyl, $NH_2$, $NH(C_1\text{-}C_4\text{-alkyl})$ or $N(C_1\text{-}C_4\text{-alkyl})(C_1\text{-}C_4\text{-alkyl})$;
$R^9$ is hydrogen, F, Cl, $OCH_3$, or $C_1\text{-}C_4$-alkyl; and
$R^{10}$ is hydrogen;
or a tautomeric, enantiomeric or diastereomeric form, or a physiologically tolerated salt of said compound.

2. The compound of the formula (I) according to claim 1, in which
$R^1$ is hydrogen,
$R^2$ is $OCH_2CH_3$, and
$R^3$ is hydrogen.

3. A compound according to claim 1, or a tautomeric, enantiomeric or diastereomeric form, or a physiologically tolerated salt of said compound, selected from the group consisting of:
5-Cyano-3-(2-ethoxyphenyl)-2-oxo-1-(quinoline-8-sulfonyl)-2,3-dihydro-1H-indol-3-yl 4-(thiazol-2-yl)piperazine-1-carboxylate;
4-(Pyridin-4-yl)piperazin-1-[5-cyano-3-(2-ethoxyphenyl)-2-oxo-1-(quinoline-8-sulfonyl)-2,3-dihydro-1H-indol-3-yl]carboxamide;
4-(Pyridin-4-yl)piperazin-1-[5-cyano-3-(2-ethoxyphenyl)-2-oxo-1-(thien-3-yl-sulfonyl)-2,3-dihydro-1H-indol-3-yl]carboxamide;
5-Cyano-3-(2-ethoxyphenyl)-2-oxo-1-(thien-3-ylsulfonyl)-2,3-dihydro-1H-indol-3-yl 4-(pyridin-4-yl)piperazine-1-carboxylate;
5-Cyano-3-(2-ethoxyphenyl)-2-oxo-1-(quinoline-8-sulfonyl)-2,3-dihydro-1H-indol-3-yl 4-(pyridin-2-yl)piperazine-1-carboxylate;
5-Cyano-3-(2-ethoxyphenyl)-2-oxo-1-(quinoline-8-sulfonyl)-2,3-dihydro-1H-indol-3-yl 4-(pyrimidin-2-yl)piperazine-1-carboxylate;
5-Cyano-3-(2-ethoxyphenyl)-2-oxo-1-(quinoline-8-sulfonyl)-2,3-dihydro-1H-indol-3-yl 4-(pyrazin-2-yl)piperazine-1-carboxylate;
5-Cyano-3-(2-ethoxyphenyl)-2-oxo-1-(thien-3-ylsulfonyl)-2,3-dihydro-1H-indol-3-yl 4-(thiazol-2-yl)piperazine-1-carboxylate;
5-Cyano-3-(2-ethoxyphenyl)-2-oxo-1-(thien-3-ylsulfonyl)-2,3-dihydro-1H-indol-3-yl 4-(5-cyanopyridin-2-yl)piperazine-1-carboxylate;
4-(5-Cyanopyridin-2-yl)piperazine-1-[5-cyano-3-(2-ethoxyphenyl)-2-oxo-1-(thien-3-ylsulfonyl)-2,3-dihydro-1H-indol-3-yl]carboxamide;
5-Cyano-3-(2-ethoxyphenyl)-2-oxo-1-(quinoline-8-sulfonyl)-2,3-dihydro-1H-indol-3-yl 4-(5-cyanopyridin-2-yl)piperazine-1-carboxylate; and
5-Cyano-3-(2-ethoxyphenyl)-2-oxo-1-(quinoline-8-sulfonyl)-2,3-dihydro-1H-indol-3-yl 4-(pyridin-4-yl)piperazine-1-carboxylate.

4. A pharmaceutical composition comprising at least one compound of the formula (I) according to claim 1, and a pharmaceutically acceptable carrier.

5. A method for the treatment of a disease in a mammal in need of such treatment, wherein the disease is selected from the group consisting of arterial hypertension, and congestive heart failure, the method comprising administering an effective amount of at least one compound according to claim 1 to said mammal.

* * * * *